United States Patent [19]

Niemann

[11] Patent Number: 4,811,832

[45] Date of Patent: Mar. 14, 1989

[54] APPARATUS FOR OBTAINING A RANDOM SAMPLE

[76] Inventor: Gary O. Niemann, 3204 E. Lake Hartridge Dr., N.W., Winter Haven, Fla. 33880

[21] Appl. No.: 776,995

[22] Filed: Sep. 17, 1985

Related U.S. Application Data

[62] Division of Ser. No. 594,379, Mar. 28, 1984, Pat. No. 4,541,290.

[51] Int. Cl.[4] ............................................. B65G 47/12
[52] U.S. Cl. .................................. 198/443; 198/690.2
[58] Field of Search ..................... 198/690.2, 698, 699, 198/397, 443, 456, 395, 453

[56] References Cited

U.S. PATENT DOCUMENTS

| | | | |
|---|---|---|---|
| 1,590,884 | 6/1926 | Bryant | 198/699 |
| 3,580,385 | 5/1971 | Thompson | 198/698 X |
| 3,712,451 | 1/1973 | Vignon | 198/397 |
| 3,986,604 | 10/1976 | Siryj | 198/395 |
| 4,198,902 | 4/1980 | Worden | 198/456 X |

Primary Examiner—Robert J. Spar
Assistant Examiner—D. Glenn Dayoan
Attorney, Agent, or Firm—Berman, Aisenberg & Platt

[57] ABSTRACT

Apparatus for obtaining a sample of objects is provided. The objects are carried by a first conveyor belt and are sampled by striking a lower surface of the conveyor belt to cause some of the objects to be thrown upwardly over a barrier into a receptacle. The objects from the receptacle are carried by a second conveyor which has cleats for separating and carrying objects to a detector one-by-one. The detector operates a deflecting plate to obtain a second sample for inspection. Objects which are not deflected by the plate are returned to the first conveyor belt, while those which are deflected enter a chute for collection. The apparatus for delivering an impact to the conveyor belt preferably comprises a bell crank which strikes the conveyor belt in response to a hydraulic actuator.

1 Claim, 5 Drawing Sheets

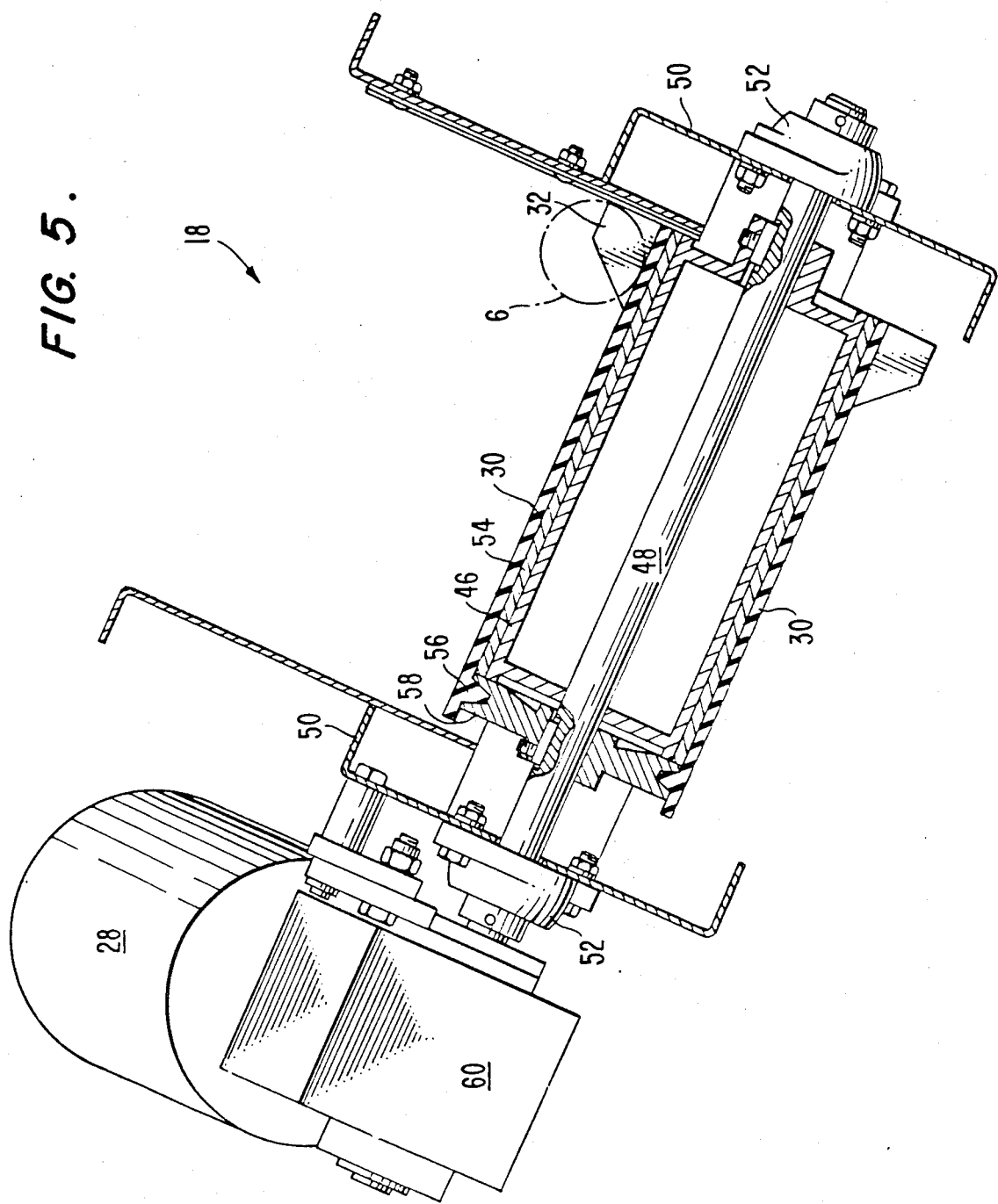

APPARATUS FOR OBTAINING A RANDOM SAMPLE

This is a division of application Ser. No. 594,379, filed Mar. 28, 1984, now U.S. Pat. No. 4,541,290.

TECHNICAL FIELD

This invention relates to the art of apparatus for obtaining a randomly selected sample from a group of objects. The invention finds particular utility in obtaining a sample of fruit.

BACKGROUND ART

In fruit harvesting, it is necessary to obtain a random sample of the harvested fruit. For example, in the harvesting of oranges, a random sample of a harvested crop is required for inspection by agricultural authorities and for inspection by the purchaser of the harvested crop. Random samples are obtained in many ways, and the most useful methods are those which cooperate with loading and bagging apparatus.

In a known random sampling system, a horizontal surface over which the harvested crop must pass has holes therein for allowing some of the fruit to fall through the holes and be collected as a sample. This arrangement is not practical because it does not allow the selection of a random sample of a predetermined size and, furthermore requires the entire horizontal surface to be covered with objects in order to obtain a truly random sample.

U.S. Pat. No. 3,672,224, (Starr) shows a sampling system where articles to be sampled are directed to a discharge chute to be sampled. U.S. Pat. No. 3,111,034 (Hostetler) shows a perforated apron at one end of a conveyor. The inspector may move holes in the apron to obtain a sample. U.S. Pat. No. 2,367,397 (Harlow) shows a sampling apparatus which employs a trapdoor through which a sample drops to a chute beneath the door.

SUMMARY OF THE INVENTION

In accordance with the invention, two sampling stations are employed in series to obtain a random sample of a predetermined size. A first sampling mechanism causes a relatively large sample to be obtained, and a second mechanism allows a random selection of a second sample of any desired size to be selected from the first sample.

The first sampling mechanism comprises an apparatus for striking the bottom of a moving conveyor belt thus causing the fruit on the conveyor belt to be bounced upwardly away from the moving conveyor belt. Since the objects were initially moving in a horizontal direction, they maintain their horizontal direction and assume a parabolic trajectory. A receptacle intercepts the objects which have assumed this trajectory and the remainder of the objects are carried by the conveyor belt to a packing station.

The striking means causes a relatively large sample of objects to be thrown into the receptacle. A second conveyor belt then carries objects from this receptacle to a second sampling station. The second conveyor belt is unique in that it provides a plurality of cleats, each of which engages a single one of the objects. This causes the objects in the first sample to move single-file into the second station.

The second station preferably includes a photocell arrangement for detecting the presence of each one of the objects and for operating a diverter door in response to electronic signals representing the presence of an object and a signal representing the ultimate size of the desired sample. For example, if it is determined to obtain a second sample comprising one-fifth of the first random sample, it is only necessary t provide signals instructing the diverter to select one of every five objects in a random fashion.

The apparatus of the invention has several advantages. There is no spillage of the objects, and nothing blocks the line of moving objects. The second conveyor carries fruit above the main conveyor to prevent the loss of elevation which accompanies some prior art samplers. Further, the inventive apparatus is compact and is easily installed on an existing conveyor.

It is an object of this invention to provide a random sampling apparatus.

It is another object of this invention to provide a random sampling apparatus having two sampling stations wherein the first sampling station provides a sample larger than that which is required in the second sampling station.

It is a still further object of this invention to provide a sampling station wherein a sample is obtained by causing objects carried by a moving conveyor to assume a trajectory away from the conveyor to thereby be separated from objects remaining on the conveyor.

It is yet another object of the invention to provide a tilted conveyor having cleats for providing a single-file flow of said objects.

BRIEF DESCRIPTION OF THE DRAWINGS

FIG. 5 is an enlarged cross-section taken along line 5—5 of FIG. 1.

DETAILED DESCRIPTION OF THE INVENTION

Figure 1:
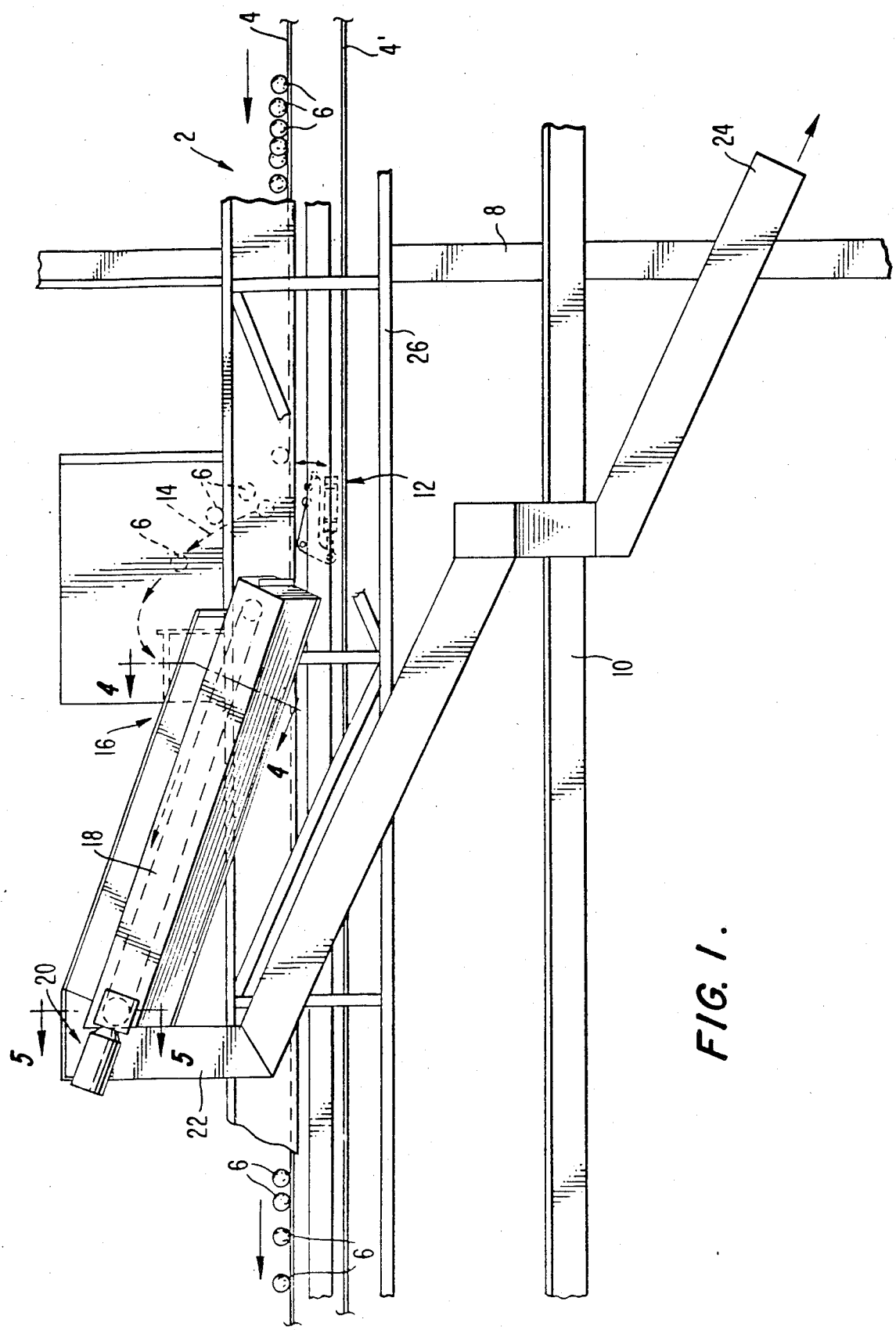
FIG. 1 is a side view of a sampling apparatus in accordance with the invention.

FIG. 1 shows a side view of a random sampling apparatus in accordance with the invention. A conveyor assembly 2, as known in the art, includes a flexible conveyor belt 4 and transports a plurality of objects 6 in a generally horizontal path. The belt is preferably continuous and a lower course 4' moves in a direction opposite to that of an upper course. The conveyor assembly 2 is supported by a frame structure 8, 10, and 26. The objects are preferably fruit.

A first sampling station 12 is located along the path of objects 6 carried by the flexible conveyor belt 4. First sampling station 12 comprises an apparatus for striking a lower surface of the flexible conveyor belt 4 to cause a plurality of the objects 6 to assume a trajectory, such as that indicated by the dashed line 14. The preferred embodiment of the striking apparatus will be described in detail below, and at this point it is only necessary to recognize that it is located between upper and lower courses of the flexible conveyor belt 4 so that it has access to a lower surface of the upper course. When the striking means engages the lower surface of the conveyor belt, some of the objects 6 are thrown upwardly, and since the objects 6 had a horizontal velocity from right to left of FIG. 1, they assume a trajectory 14. The objects 6 which are not thrown upwardly by the impact of the striking means are carried along the conveyor assembly 2 for further processing.

A receptacle 16 extends across belt 4 and gathers objects by intersecting the trajectory 14 to thus separate a first sample of objects 6.

The first sample received in receptacle 16 is directed to a second conveyor 18 and carried one-by-one into a second sampling station 20. At the second sampling station 20, a predetermined number of the objects 6 are directed into a chute 22, and the remainder is returned to the flexible conveyor belt 4. Objects representing the final sample are directed into chute 22 and collected at discharge end 24.

Figure 2:
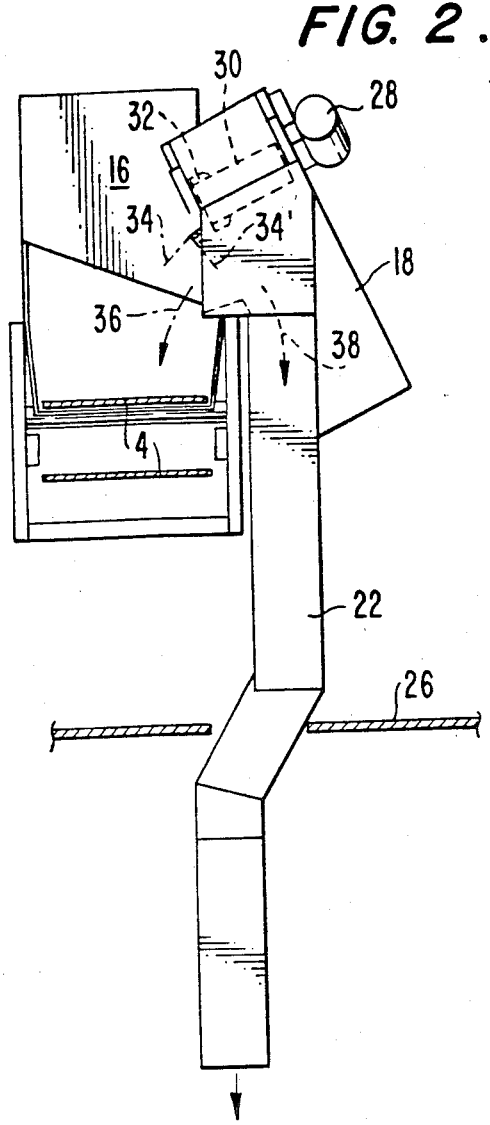
FIG. 2 is an end view of the apparatus shown in FIG. 1.

FIG. 2 is an end view of the apparatus of FIG. 1, except that supporting frame members 8 and 10 have been omitted and the frame member 26 is partially shown. The upper end of second conveyor 18 includes a drive motor 28 for driving a second conveyor belt 30. Cleats 32 are attached to a lower edge of the second conveyor belt 30 for a purpose which will be described in more detail below. At this point, it is sufficient to point out that the second conveyor belt 30 is tilted and that cleats 32 produce a single-file line of objects 6 from the first sampling station 12. A diverting plate 34 is shown in two positions in FIG. 2. In a first position, the plate allows objects to follow the path indicated by arrow 36 to thereby return them to the flexible conveyor belt 4. In the second position, indicated by the reference numeral 34', the diverting plate causes objects 6 to enter the chute 22 as indicated by the arrow 38. The operation of plate 34 will be more fully described below.

Figure 3:
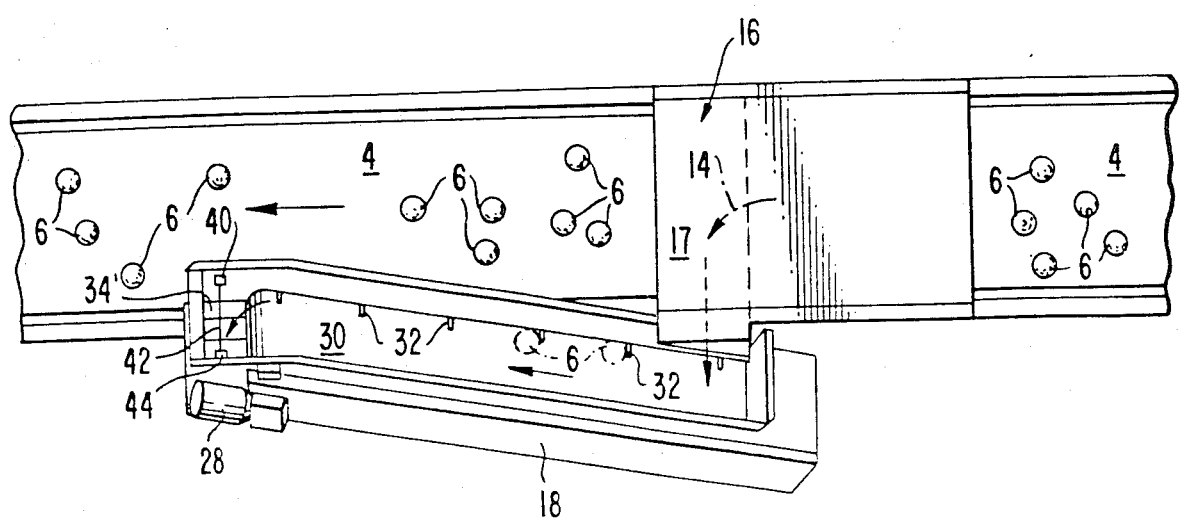
FIG. 3 is a top view of the apparatus shown in FIG. 1.

FIG. 3 is a top view of the apparatus in accordance with the invention. This figure shows the trajectory 14 which causes fruit to be received in a receptacle 16 and carried by a tilted tray 17 into a lower end of the second conveyor 18. Cleats 32 are of such a size and shape that only a single object 6 is engaged by each cleat. At the upper, or discharge, end 20 of second conveyor 18 is a detection apparatus for determining the presence of an object 6 at the discharge end. In the preferred embodiment, the detection apparatus includes a light source and photodetector 40 which directs a narrow beam of light 42 across the upper end of the second conveyor and receives light from retroreflector 44. The presence of an object 6 is detected by a change in the voltage level produced by the photodetector as a result of an object 6 blocking the beam 42. It will be appreciated that many kinds of detection apparatus may be employed to accomplish the same purpose.

Figure 4:
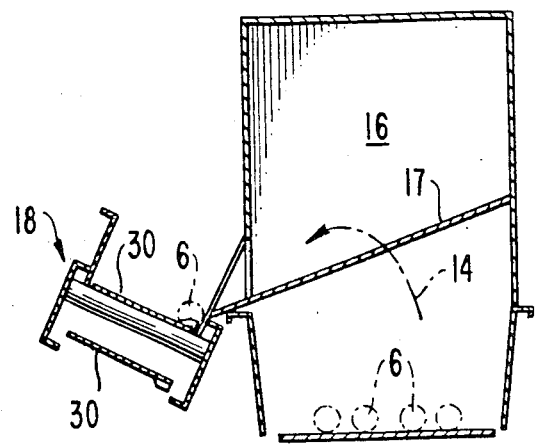
FIG. 4 is a cross-section taken along line 4—4 of FIG. 1.

FIG. 4 is a cross-section taken along line 4—4 of FIG. 1 and shows the receptacle 16 and tray 17 which receive objects 6 from the first sampling station 12.

FIG. 5 is an enlarged cross-section taken along line 5—5 of FIG. 1. This figure shows in some detail the preferred construction of the second conveyor 18. A second conveyor belt 30 is made of flexible material and is a continuous belt. Belt 30 is driven by a drive cylinder 46 which is secured to a shaft 48. The shaft is supported at opposite ends of a housing 50 by bearings 52. Drive cylinder 46 preferably is covered with a friction material 54 to assist in transferring force from the cylinder 46 to the second conveyor belt 30. In addition, a V-shaped protrusion 56 engages a pulley 58 which is also secured to the shaft 48 for driving the second conveyor belt 30. Shaft 48 is operatively connected to drive motor 28 by a gearbox 60.

Second conveyor belt 30 has cleats 32 along a lower edge thereof for engaging individual objects 6. The cleats are preferably thin, tapered elements and a broader portion engages a single object 6 while a tapered portion prevents more than one object from being engaged.

Second conveyor belt 30 is tilted about a horizontal axis in two directions. First, it is tilted in a longitudinal direction as shown in FIG. 1 and secondly, it is tilted in a lateral direction as shown in FIG. 5. The longitudinal tilt is preferably about 20 degrees and the lateral tilt is preferably about 25 degrees, each with respect to a horizontal direction.

While the second conveyor is shown in the figures carrying objects in the same direction as those of conveyor 4, it will be appreciated that it could carry the objects in an opposite direction.

Figure 6:
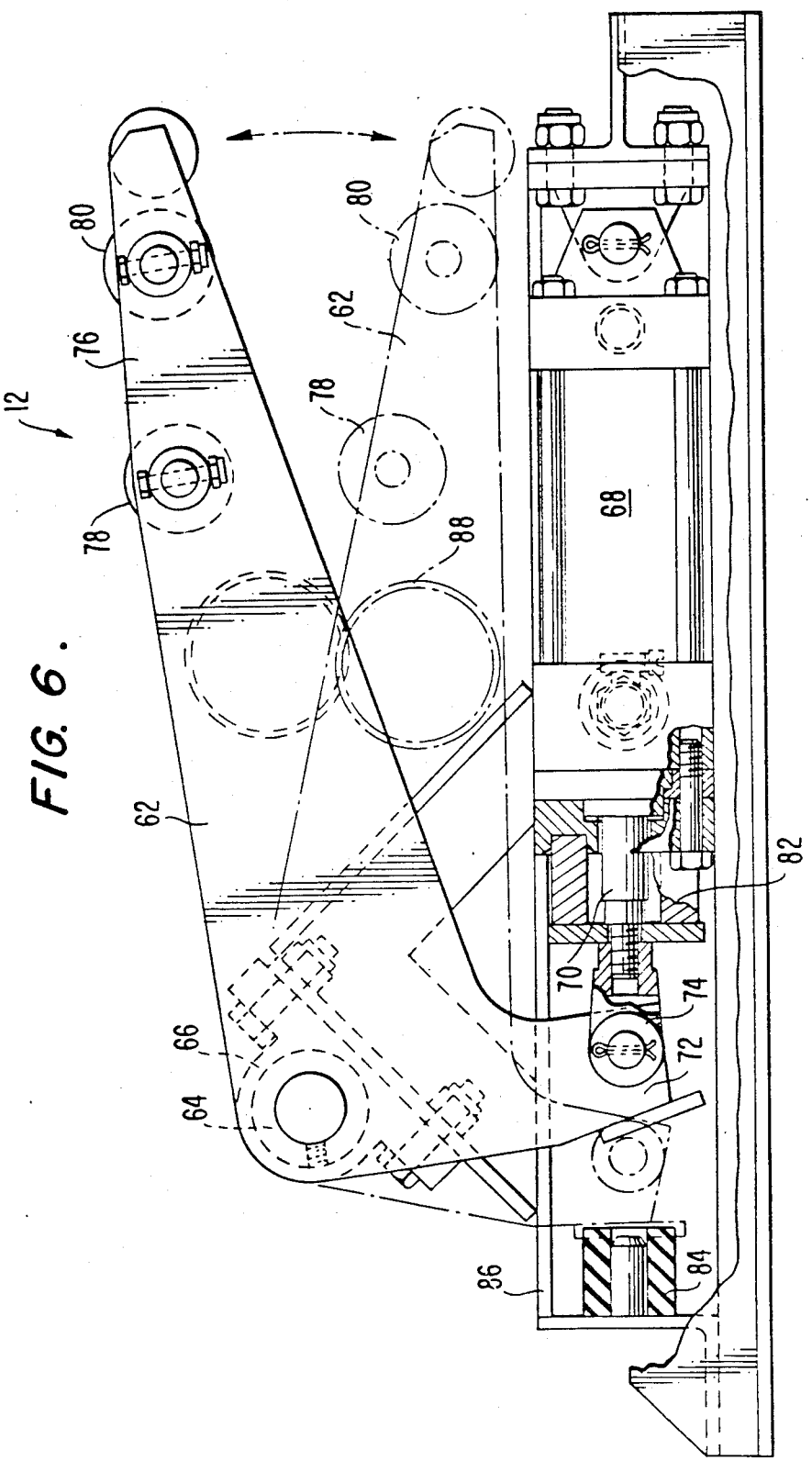
FIG. 6 is a side view of an impact apparatus in accordance with the invention.
Figure 7:
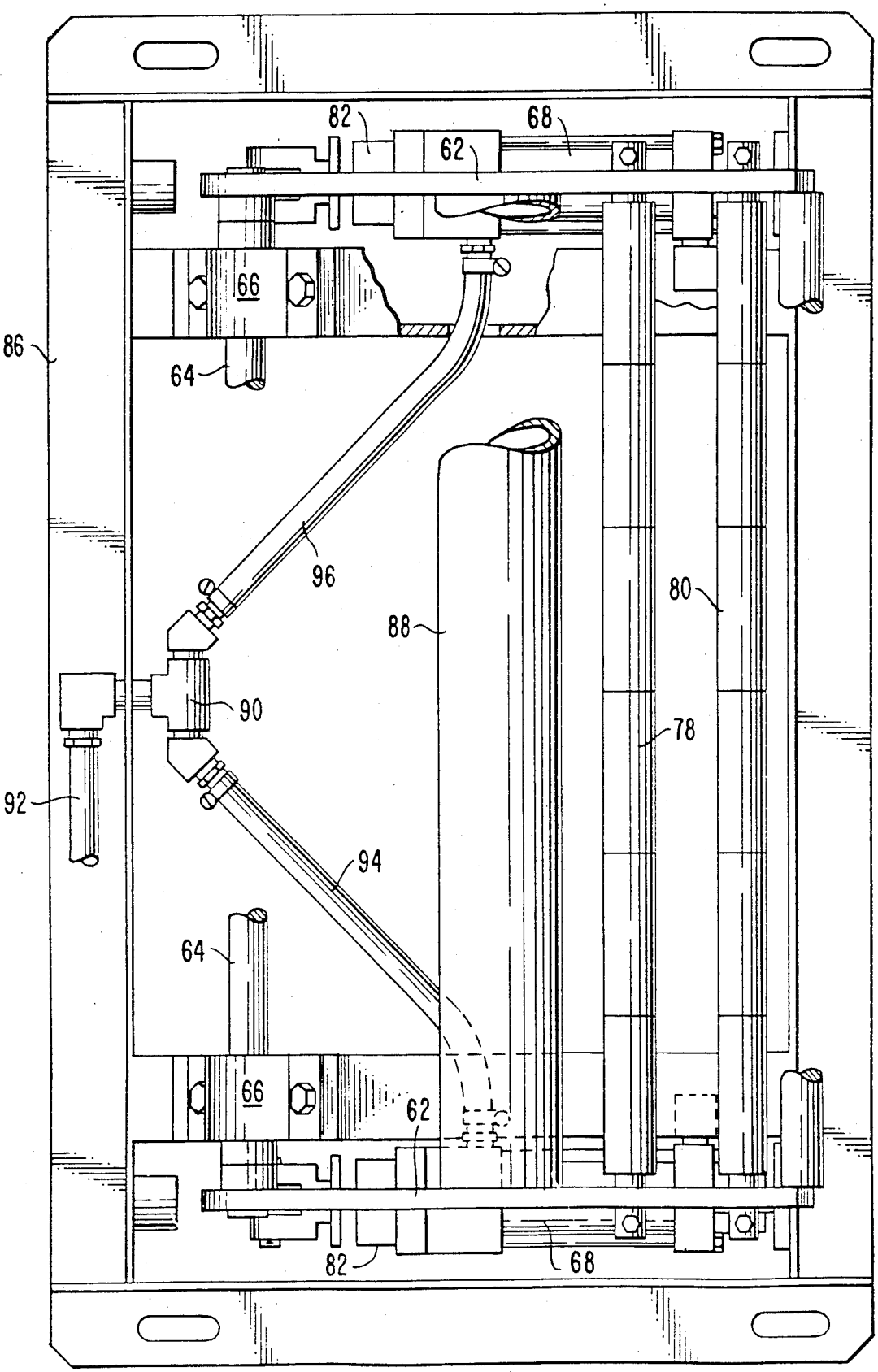
FIG. 7 is a top view of the impact apparatus shown in FIG. 6.

FIGS. 6 and 7 are enlarged views of the preferred striking means used in the first sampling station 12 for causing objects 6 to assume the trajectory 14. Two bell cranks 62 (one of which shows in FIG. 6) are mounted to a common shaft 64. The shaft is carried by bearings 66. A hydraulic actuator 68 has an actuating shaft 70 which is connected to an end 72 of the bell crank 62 by clevis 74. The hydraulic actuator 68 is energized to control the actuating shaft 70 thus causing bell crank 62 to pivot about the pivotal connection provided by the bearings 66. A second end 76 of the bell crank 62 is adapted to engage the lower surface of flexible conveyor belt 4 when in the position shown in solid lines in FIG. 6. Rollers 78, 80 are connected between bell cranks 62 to provide a reduced-friction contact with the conveyor belt 4. The bell cranks 62 are preferably aligned with the direction of movement of the conveyor belt 4, as shown in FIG. 1, so that engagement with the belt does no damage but only causes the roller 78, 80 to rotate.

A first bumper 82 is located on actuator 68 to absorb shock created when bell cranks 62 assume the position shown in solid lines in FIG. 6 wherein the bell cranks 62 are striking the conveyor belt 4. A second bumper 84 is located on a housing 86 and engages the end 72 of the bell cranks 62 when in the position shown in dashed lines.

FIG. 7 is a top view of the striking apparatus shown in FIG. 6. A large tubular member 88 connects bell cranks 62 to insure their operation together. In the preferred embodiment, the actuators 68 are air-operated and air is supplied to a connector 90 by a hose 92. Separate supply pipes 94, 96 carry fluid from the connector 90 to respective actuators 68. Of course, the actuators may be of any form, for example, they may be electrically operated solenoids.

In operation, fruit, for example, oranges, is loaded onto the flexible conveyor belt 4 and thereby carried into the first sampling station 12. The bell crank striking apparatus is programmed to apply an impulse to the lower side of conveyor belt 4 at random or predetermined intervals to cause a first sample of fruit to be thrown upwardly into the receptacle 16. The first sample of fruit flows into the lower end of second conveyor 18 which then carries single pieces of fruit upwardly to the second sampling station 20. The cooperation of the tilted conveyor belt 30 and the cleats 32 causes only individual pieces of fruit to be carried to station 20. Detecting means determines the presence of a piece of fruit and supplies information to a circuit of conventional design which also receives information regarding the size of the sample desired to be taken. Output signals from the circuit control the operation of diverter plate 34 and either causes fruit to be deflected into chute 22 or allowed to return to the conveyor 4. Fruit which has been deflected to chute 22 is then collected at the output end 24 for inspection.

It will be appreciated that the apparatus in accordance with the invention efficiently samples objects by first taking a large random sample and then obtaining a second random sample from the first. Modifications of the apparatus within the scope of the appended claims will be apparent to those of skill in the art.

What is claimed is:

1. Apparatus for feeding a plurality of objects one at a time comprising a surface having a plurality of movable cleats mounted on said surface along on edge thereof and a wall adjacent said one edge and stationary with respect to said cleats, said surface being mounted such that said cleats move in a first direction which is upwardly inclined with respect to a horizontal direction and said surface is tilted about said first direction so that said one edge is lower than an opposed edge, each of said cleats extending only partially across said surface and having a width and height adequate normally to engage only a single of said objects and small enough to reject objects other than said single of said objects, each of said cleats being adjacent said one edge and spaced from an opposed edge, whereby each of said cleats engages a single of said objects, rejects all of a plurality of objects except said single object, and carries said single of said objects by movement of said cleats in said first direction.

* * * * *